United States Patent
Yue et al.

(10) Patent No.: US 11,116,514 B2
(45) Date of Patent: Sep. 14, 2021

(54) SURGICAL CLIP APPLIER WITH USER FEEDBACK FEATURE

(71) Applicant: Covidien LP, Mansfield, MA (US)

(72) Inventors: Xin Yue, Shanghai (CN); Xiaolin Sang, Shanghai (CN); Encheng Hu, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 316 days.

(21) Appl. No.: 16/349,304

(22) PCT Filed: Feb. 6, 2017

(86) PCT No.: PCT/CN2017/072960
§ 371 (c)(1),
(2) Date: May 13, 2019

(87) PCT Pub. No.: WO2018/141110
PCT Pub. Date: Aug. 9, 2018

(65) Prior Publication Data
US 2020/0178979 A1    Jun. 11, 2020

(51) Int. Cl.
*A61B 17/128*    (2006.01)

(52) U.S. Cl.
CPC .............................. *A61B 17/1285* (2013.01)

(58) Field of Classification Search
CPC ... A61B 17/1285; A61B 17/068; A61B 17/10; A61B 17/2909; A61B 17/128; A61B 17/28; A61B 17/29
See application file for complete search history.

(56) References Cited

U.S. PATENT DOCUMENTS

| | | |
|---|---|---|
| 3,120,230 A | 2/1964 | Skold |
| 3,363,628 A | 1/1968 | Wood |
| | (Continued) | |

FOREIGN PATENT DOCUMENTS

| | | |
|---|---|---|
| AU | 2013254887 A1 | 11/2013 |
| CA | 1163889 A | 3/1984 |
| | (Continued) | |

OTHER PUBLICATIONS

International Search Report for PCT/CN2017/072960 date of completion is Nov. 2, 2017 (2 pages).
(Continued)

*Primary Examiner* — Kathleen S Holwerda
*Assistant Examiner* — Brooke Labranche

(57) ABSTRACT

A surgical clip applier (100) includes a handle assembly (110) having a housing (118), a trigger (114), and an advancing mechanism supported in the housing (118) and being actuatable by the trigger (114). An elongated tube assembly (200) extends from the housing (118). A first shaft (202) is slidably disposed within the elongated tube assembly (200) and defines a surface portion (203). A second shaft (215) is disposed through an outer surface of the elongated tube assembly (200) and is in operative engagement with the surface portion (203) of the first shaft (202). Upon actuating the advancing mechanism, the first shaft (202) moves distally within the elongated tube assembly (200) relative to the second shaft (215) such that the surface portion (203) of the first shaft (202) traverses the second shaft (215) to produce at least one of an audible or tactile feedback.

24 Claims, 7 Drawing Sheets

(56) References Cited

U.S. PATENT DOCUMENTS

| | | |
|---|---|---|
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |

(56) References Cited

U.S. PATENT DOCUMENTS

| | | |
|---|---|---|
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,543 A | 12/1997 | Burdorff |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sheds et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |

(56) References Cited

U.S. PATENT DOCUMENTS

| | | | |
|---|---|---|---|
| 6,562,051 | B1 | 5/2003 | Bolduc et al. |
| 6,569,171 | B2 | 5/2003 | DeGuillebon et al. |
| 6,579,304 | B1 | 6/2003 | Hart et al. |
| 6,599,298 | B1 | 7/2003 | Forster et al. |
| 6,602,252 | B2 | 8/2003 | Mollenauer |
| 6,607,540 | B1 | 8/2003 | Shipp |
| 6,613,060 | B2 | 9/2003 | Adams et al. |
| 6,626,916 | B1 | 9/2003 | Yeung et al. |
| 6,626,922 | B1 | 9/2003 | Hart et al. |
| 6,648,898 | B1 | 11/2003 | Baxter |
| 6,652,538 | B2 | 11/2003 | Kayan et al. |
| 6,652,539 | B2 | 11/2003 | Shipp et al. |
| 6,656,193 | B2 | 12/2003 | Grant et al. |
| 6,673,083 | B1 | 1/2004 | Kayan |
| 6,676,659 | B2 | 1/2004 | Hutchins et al. |
| 6,679,894 | B2 | 1/2004 | Damarati |
| RE38,445 | E | 2/2004 | Pistl et al. |
| 6,695,854 | B1 | 2/2004 | Kayan et al. |
| 6,706,057 | B1 | 3/2004 | Bidoia et al. |
| 6,716,226 | B2 | 4/2004 | Sixto, Jr. et al. |
| 6,723,109 | B2 | 4/2004 | Solingen |
| 6,733,514 | B2 | 5/2004 | Miser |
| 6,743,240 | B2 | 6/2004 | Smith et al. |
| 6,743,241 | B2 | 6/2004 | Kerr |
| 6,773,438 | B1 | 8/2004 | Knodel et al. |
| 6,773,440 | B2 | 8/2004 | Gannoe et al. |
| 6,776,783 | B1 | 8/2004 | Frantzen et al. |
| 6,776,784 | B2 | 8/2004 | Ginn |
| 6,780,195 | B2 | 8/2004 | Porat |
| 6,793,663 | B2 | 9/2004 | Kneifel et al. |
| 6,793,664 | B2 | 9/2004 | Mazzocchi et al. |
| 6,802,848 | B2 | 10/2004 | Anderson et al. |
| 6,814,742 | B2 | 11/2004 | Kimura et al. |
| 6,818,009 | B2 | 11/2004 | Hart et al. |
| 6,821,273 | B2 | 11/2004 | Mollenauer |
| 6,821,284 | B2 | 11/2004 | Sturtz et al. |
| 6,821,285 | B2 | 11/2004 | Laufer et al. |
| 6,824,547 | B2 | 11/2004 | Wilson, Jr. et al. |
| 6,824,548 | B2 | 11/2004 | Smith et al. |
| 6,835,199 | B2 | 12/2004 | McGuckin, Jr. et al. |
| 6,835,200 | B2 | 12/2004 | Laufer et al. |
| 6,837,893 | B2 | 1/2005 | Miller |
| 6,837,894 | B2 | 1/2005 | Pugsley, Jr. et al. |
| 6,837,895 | B2 | 1/2005 | Mayenberger |
| 6,840,945 | B2 | 1/2005 | Manetakis et al. |
| 6,843,794 | B2 | 1/2005 | Sixto, Jr. et al. |
| 6,849,078 | B2 | 2/2005 | Durgin et al. |
| 6,849,079 | B1 | 2/2005 | Blake, III et al. |
| 6,853,879 | B2 | 2/2005 | Sunaoshi |
| 6,869,435 | B2 | 3/2005 | Blake, III |
| 6,869,436 | B2 | 3/2005 | Wendlandt |
| 6,889,116 | B2 | 5/2005 | Jinno |
| 6,896,676 | B2 | 5/2005 | Zubok et al. |
| 6,896,682 | B1 | 5/2005 | McClellan et al. |
| 6,896,684 | B2 | 5/2005 | Monassevitch et al. |
| 6,905,503 | B2 | 6/2005 | Gifford, III et al. |
| 6,911,032 | B2 | 6/2005 | Jugenheimer et al. |
| 6,911,033 | B2 | 6/2005 | de Guillebon et al. |
| 6,913,607 | B2 | 7/2005 | Ainsworth et al. |
| 6,916,327 | B2 | 7/2005 | Northrup, III et al. |
| 6,916,332 | B2 | 7/2005 | Adams |
| 6,923,818 | B2 | 8/2005 | Muramatsu et al. |
| 6,939,356 | B2 | 9/2005 | Debbas |
| 6,942,674 | B2 | 9/2005 | Belef |
| 6,942,676 | B2 | 9/2005 | Buelna |
| 6,945,978 | B1 | 9/2005 | Hyde |
| 6,945,979 | B2 | 9/2005 | Kortenbach et al. |
| 6,949,107 | B2 | 9/2005 | McGuckin, Jr. et al. |
| 6,953,465 | B2 | 10/2005 | Dieck et al. |
| 6,955,643 | B2 | 10/2005 | Gellman et al. |
| 6,959,852 | B2 | 11/2005 | Shelton, IV et al. |
| 6,960,218 | B2 | 11/2005 | Rennich |
| 6,960,221 | B2 | 11/2005 | Ho et al. |
| 6,962,594 | B1 | 11/2005 | Thevenet |
| 6,963,792 | B1 | 11/2005 | Green |
| 6,964,363 | B2 | 11/2005 | Wales et al. |
| 6,964,668 | B2 | 11/2005 | Modesitt et al. |
| 6,966,875 | B1 | 11/2005 | Longobardi |
| 6,966,917 | B1 | 11/2005 | Suyker et al. |
| 6,966,919 | B2 | 11/2005 | Sixto, Jr. et al. |
| 6,969,391 | B1 | 11/2005 | Gazzani |
| 6,972,023 | B2 | 12/2005 | Whayne et al. |
| 6,972,027 | B2 | 12/2005 | Fallin et al. |
| 6,973,770 | B2 | 12/2005 | Schnipke et al. |
| 6,974,462 | B2 | 12/2005 | Sater |
| 6,974,466 | B2 | 12/2005 | Ahmed et al. |
| 6,974,475 | B1 | 12/2005 | Wall |
| 6,981,505 | B2 | 1/2006 | Krause et al. |
| 6,981,628 | B2 | 1/2006 | Wales |
| 6,991,635 | B2 | 1/2006 | Takamoto et al. |
| 7,001,399 | B2 | 2/2006 | Damarati |
| 7,037,315 | B2 | 5/2006 | Sancoff et al. |
| 7,041,119 | B2 | 5/2006 | Green |
| 7,052,504 | B2 | 5/2006 | Hughett |
| 7,056,330 | B2 | 6/2006 | Gayton |
| 7,070,602 | B2 | 7/2006 | Smith et al. |
| 7,108,700 | B2 | 9/2006 | Chan |
| 7,108,703 | B2 | 9/2006 | Danitz et al. |
| 7,141,056 | B2 | 11/2006 | Manetakis |
| 7,144,402 | B2 | 12/2006 | Kuester, III |
| 7,175,648 | B2 | 2/2007 | Nakao |
| 7,179,265 | B2 | 2/2007 | Manetakis et al. |
| 7,207,997 | B2 | 4/2007 | Shipp et al. |
| 7,211,091 | B2 | 5/2007 | Fowler et al. |
| 7,211,092 | B2 | 5/2007 | Hughett |
| 7,213,736 | B2 | 5/2007 | Wales et al. |
| 7,214,230 | B2 | 5/2007 | Brock et al. |
| 7,214,232 | B2 | 5/2007 | Bowman et al. |
| 7,223,271 | B2 | 5/2007 | Muramatsu et al. |
| 7,223,272 | B2 | 5/2007 | Francese et al. |
| 7,232,445 | B2 | 6/2007 | Kortenbach et al. |
| 7,238,191 | B2 | 7/2007 | Bachmann |
| 7,261,724 | B2 | 8/2007 | Molitor et al. |
| 7,261,725 | B2 | 8/2007 | Binmoeller |
| 7,264,625 | B1 | 9/2007 | Buncke |
| 7,288,098 | B2 | 10/2007 | Huitema et al. |
| 7,297,149 | B2 | 11/2007 | Vitali et al. |
| 7,312,188 | B2 | 12/2007 | Kiso |
| 7,316,693 | B2 | 1/2008 | Viola |
| 7,316,696 | B2 | 1/2008 | Wilson, Jr. et al. |
| 7,322,995 | B2 | 1/2008 | Buckman et al. |
| 7,326,223 | B2 | 2/2008 | Wilson, Jr. |
| 7,329,266 | B2 | 2/2008 | Royse et al. |
| 7,331,968 | B2 | 2/2008 | Arp et al. |
| 7,338,503 | B2 | 3/2008 | Rosenberg et al. |
| 7,357,805 | B2 | 4/2008 | Masuda et al. |
| 7,367,939 | B2 | 5/2008 | Smith et al. |
| 7,407,074 | B2 | 8/2008 | Ortiz et al. |
| 7,419,495 | B2 | 9/2008 | Menn et al. |
| 7,422,137 | B2 | 9/2008 | Manzo |
| 7,431,724 | B2 | 10/2008 | Manetakis et al. |
| 7,452,327 | B2 | 11/2008 | Durgin et al. |
| 7,485,124 | B2 | 2/2009 | Kuhns et al. |
| 7,488,335 | B2 | 2/2009 | Sgro |
| 7,510,562 | B2 | 3/2009 | Lindsay |
| 7,552,853 | B2 | 6/2009 | Mas et al. |
| 7,559,937 | B2 | 7/2009 | de la Torre et al. |
| 7,572,266 | B2 | 8/2009 | Young et al. |
| 7,578,827 | B2 | 8/2009 | Gadberry et al. |
| 7,582,095 | B2 | 9/2009 | Shipp et al. |
| 7,585,304 | B2 | 9/2009 | Hughett |
| 7,615,058 | B2 | 11/2009 | Sixto, Jr. et al. |
| 7,615,060 | B2 | 11/2009 | Stokes et al. |
| 7,621,926 | B2 | 11/2009 | Wixey et al. |
| 7,637,917 | B2 | 12/2009 | Whitfield et al. |
| 7,644,848 | B2 | 1/2010 | Swayze et al. |
| 7,686,820 | B2 | 3/2010 | Huitema et al. |
| 7,695,482 | B2 | 4/2010 | Viola |
| 7,717,926 | B2 | 5/2010 | Whitfield et al. |
| 7,727,247 | B2 | 6/2010 | Kimura et al. |
| 7,727,248 | B2 | 6/2010 | Smith et al. |
| 7,731,724 | B2 | 6/2010 | Huitema et al. |
| 7,731,725 | B2 | 6/2010 | Gadberry et al. |
| 7,736,388 | B2 | 6/2010 | Goldfarb et al. |

(56) References Cited

U.S. PATENT DOCUMENTS

| | | |
|---|---|---|
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,861,906 B2 | 1/2011 | Doll |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huiterna et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,828,023 B2 | 9/2014 | Neff et al. |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |

(56) References Cited

U.S. PATENT DOCUMENTS

| | | |
|---|---|---|
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,750,503 B2 | 9/2017 | Milliman |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0085015 A1 | 4/2006 | Whitfield et al. |
| 2006/0100649 A1 | 5/2006 | Hart |
| 2006/0163312 A1 | 7/2006 | Viola et al. |
| 2006/0173470 A1 | 8/2006 | Dray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0045981 A1 | 2/2008 | Margolin et al. |
| 2008/0051808 A1 | 2/2008 | Rivera et al. |

(56) References Cited

U.S. PATENT DOCUMENTS

| | | |
|---|---|---|
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0209946 A1 | 8/2009 | Swayze et al. |
| 2009/0228023 A1 | 9/2009 | Cui |
| 2009/0326558 A1 | 12/2009 | Cui et al. |
| 2010/0049216 A1 | 2/2010 | Zergiebel |
| 2010/0274264 A1 | 10/2010 | Schulz et al. |
| 2010/0318103 A1 | 12/2010 | Cheng et al. |
| 2011/0028994 A1 | 2/2011 | Whitfield et al. |
| 2011/0054498 A1 | 3/2011 | Monassevitch et al. |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0131697 A1 | 5/2013 | Hartoumbekis |
| 2013/0165951 A1 | 6/2013 | Blake, III |
| 2013/0172929 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2014/0074143 A1 | 3/2014 | Fitzgerald et al. |
| 2014/0263565 A1 | 9/2014 | Lytle, IV et al. |
| 2014/0276970 A1 | 9/2014 | Messerly et al. |
| 2015/0032131 A1 | 1/2015 | Sorrentino et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0189132 A1* | 7/2017 | Adams ............... A61B 90/08 |
| 2017/0238936 A1 | 8/2017 | Mujawar |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |

FOREIGN PATENT DOCUMENTS

| | | |
|---|---|---|
| CN | 101507629 A | 8/2009 |
| CN | 104337558 A | 2/2015 |
| CN | 104605911 B | 2/2017 |
| DE | 20 2005 001664 U1 | 5/2005 |
| DE | 202007003398 U1 | 6/2007 |
| DE | 202009006113 U1 | 7/2009 |
| EP | 0000756 A1 | 2/1979 |
| EP | 0406724 A1 | 1/1991 |
| EP | 0514139 A2 | 11/1992 |
| EP | 0732078 A2 | 9/1996 |
| EP | 1769757 A1 | 4/2007 |
| EP | 2671611 A1 | 12/2013 |
| GB | 2073022 A | 10/1981 |
| JP | 2003033361 A | 2/2003 |
| JP | 2006154230 A | 6/2006 |
| JP | 2006277221 A | 10/2006 |
| JP | 2008017876 A | 1/2008 |
| WO | WO9925265 A1 | 5/1999 |
| WO | 0042922 A1 | 7/2000 |
| WO | 0166001 A2 | 9/2001 |
| WO | 0167965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |

OTHER PUBLICATIONS

Extended European Search Report dated Dec. 17, 2020 corresponding to counterpart Patent Application EP 17895153.9.
European Office Action corresponding to EP 12 152 989.5 dated May 4, 2015.
Australian Office Action corresponding to AU 2009212759 dated May 7, 2015.
Chinese Office Action corresponding to Int'l Appln No. CN 201210212642.9 dated Jun. 3, 2015.
European Office Action corresponding to Int'l Appln No. EP 04 719 757.9 dated Jun. 12, 2015.
European Office Action corresponding to Int'l Appln No. EP 13 166 382.5 dated Jun. 19, 2015.
Japanese Office Action corresponding to Int'l Application No. JP 2010-226908 dated Jun. 26, 2015.
Extended European Search Report corresponding to Int'l Application No. EP 15 15 5024A dated Jul. 17, 2015.
Extended European Search Report corresponding to Int'l Application No. EP 14 19 2026.4 dated Jul. 17, 2015.
Japanese Office Action corresponding to Int'l Application No. JP 2011-160126 dated Aug. 10, 2015.
Extended European Search Report corresponding to Int'l Application No. EP 14 15 0321.9 dated Sep. 23, 2015.
Extended European Search Report corresponding to Int'l Application No. EP 11 25 0675.3 dated Oct. 7, 2015.

(56) References Cited

OTHER PUBLICATIONS

Extended European Search Report corresponding to Int'l Application No. EP 11 25 0674.6 dated Oct. 7, 2015.
Extended European Search Report corresponding to Int'l Application No. EP 12 19 3447.5 dated Oct. 19, 2015.
Canadian Office Action corresponding to Int'l Application No. CA 2,675,875 dated Oct. 26, 2015.
Japanese Office Action corresponding to Int'l Application No. JP 2015-005629 dated Oct. 28, 2015.
Japanese Office Action corresponding to Int'l Application No. JP 2014-245081 dated Oct. 28, 2015.
Canadian Office Action corresponding to Int'l Application No. CA 2,675,921 dated Oct. 30, 2015.
Chinese Office Action corresponding to Int'l Application No. CN 201210555570.8 dated Nov. 2, 2015.
Canadian Office Action corresponding to Int'l Application No. CA 2,676,309 dated Nov. 3, 2015.
Canadian Office Action corresponding to Int'l Application No. Ca 2,676,211 dated Nov. 24, 2015.
Canadian Office Action corresponding to Int'l Application No. CA 2,676,547 dated Nov. 25, 2015.
Extended European Search Report corresponding to Int'l Application No. EP 15 17 3809.3 dated Nov. 25, 2015.
Chinese Office Action corresponding to Int'l Application No. CN 201210586814.9 dated Dec. 2, 2015.
Extended European Search Report corresponding to Int'l Application No. EP 12 17 2940.4 dated Dec. 14, 2015.
Chinese First Office Action corresponding to Int'l Appln. No. CN 201210586826A dated Dec. 30, 2015.
Extended European Search Report corresponding to Int'l Appln. No. EP 15 18 5362.9 dated Feb. 12, 2016.
Extended European Search Report corresponding to Int'l Appln. No. EP 12 19 7813.4 dated Mar. 7, 2016.
Canadian Office Action corresponding to Int'l Appln. No. CA 2,676,465 dated Mar. 8, 2016.
Japanese Office Action corresponding to Int'l Appln. No. JP 2014-245081 dated Mar. 18, 2016.
Japanese Office Action corresponding to Int'l Appln. No. JP 2015-005629 dated Mar. 18, 2016.
Extended European Search Report corresponding to Int'l Appln. No. EP 15 19 3549.1 dated Mar. 22, 2016.
International Search Report and Written Opinion corresponding to Int'l Appln. No. PCT/CN2015/082199 dated Mar. 31, 2016.
Extended European Search Report corresponding to Int'l Appln. No. EP 15 19 7251.0 dated Apr. 8, 2016.
Extended European Search Report corresponding to Int'l Appln. No. EP 16 15 0739.7 dated May 17, 2016.
Canadian Office Action corresponding to Int'l Appln. No. CA 2,716,672 dated May 31, 2016.
Canadian Office Action corresponding to Int'l Appln. No. CA 2,717,448 dated May 31, 2016.
Canadian Office Action corresponding to Int'l Appln. No. CA 2,721,951 dated Jun. 1, 2016.
Partial European Search Report corresponding to Int'l Appln. No. EP 16 15 0287.7 dated Jun. 16, 2016.
Chinese Second Office Action corresponding to Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
Extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 7, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).

(56) References Cited

OTHER PUBLICATIONS

The extended European Search Report corresponding to European Application No. EP 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. Ep 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.

* cited by examiner

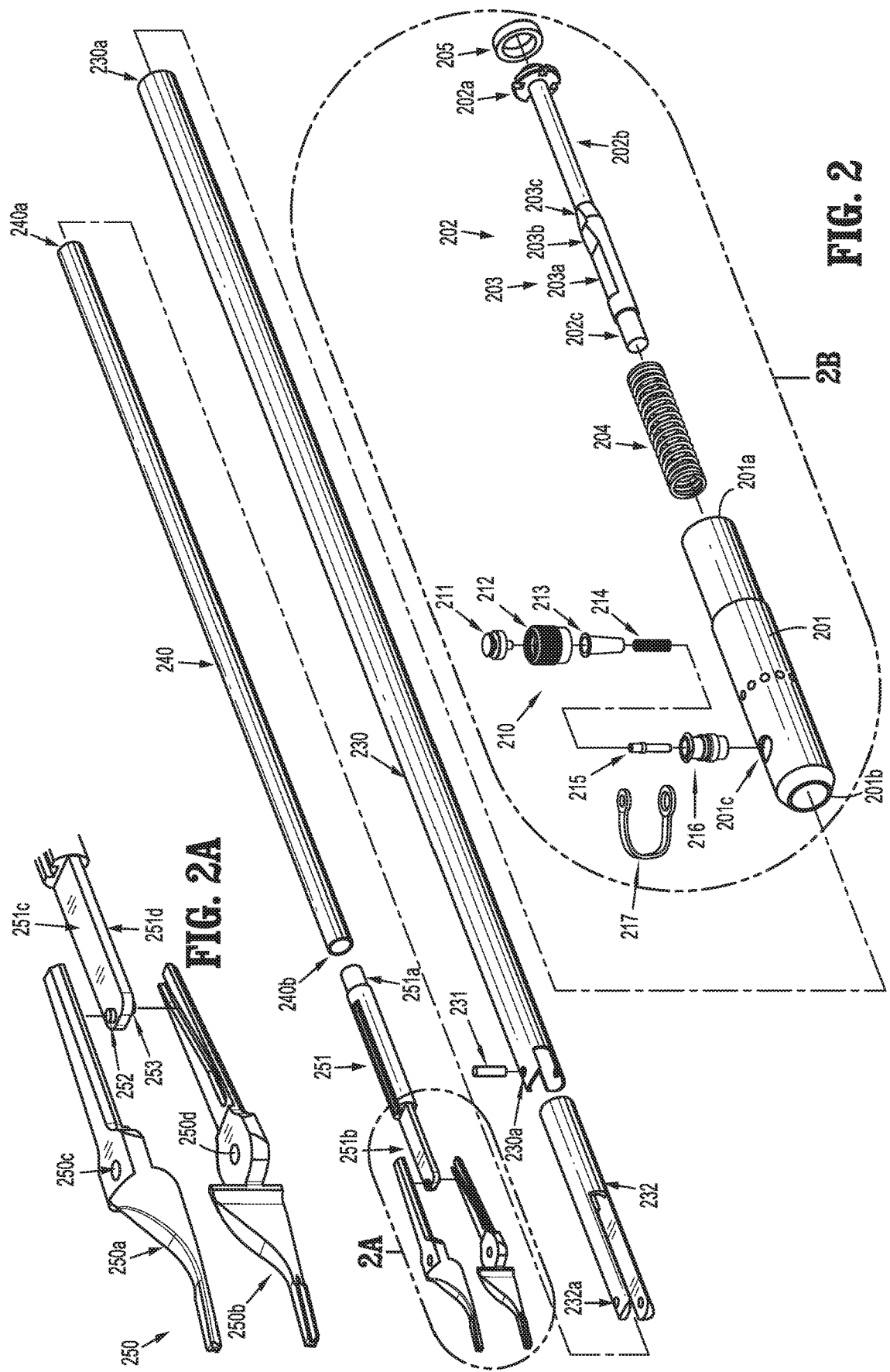

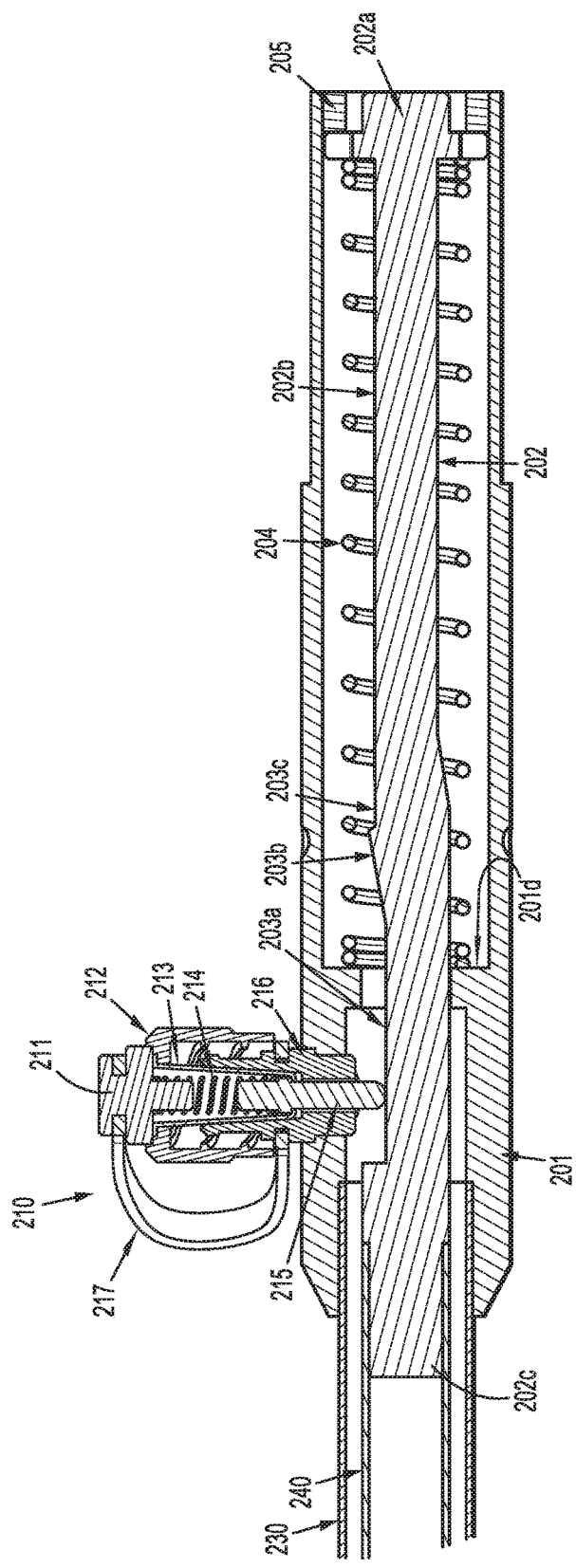
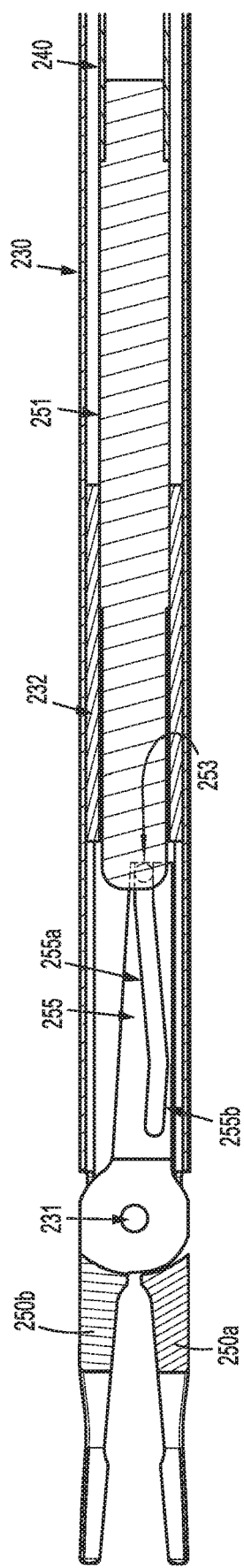
FIG. 5
FIG. 6

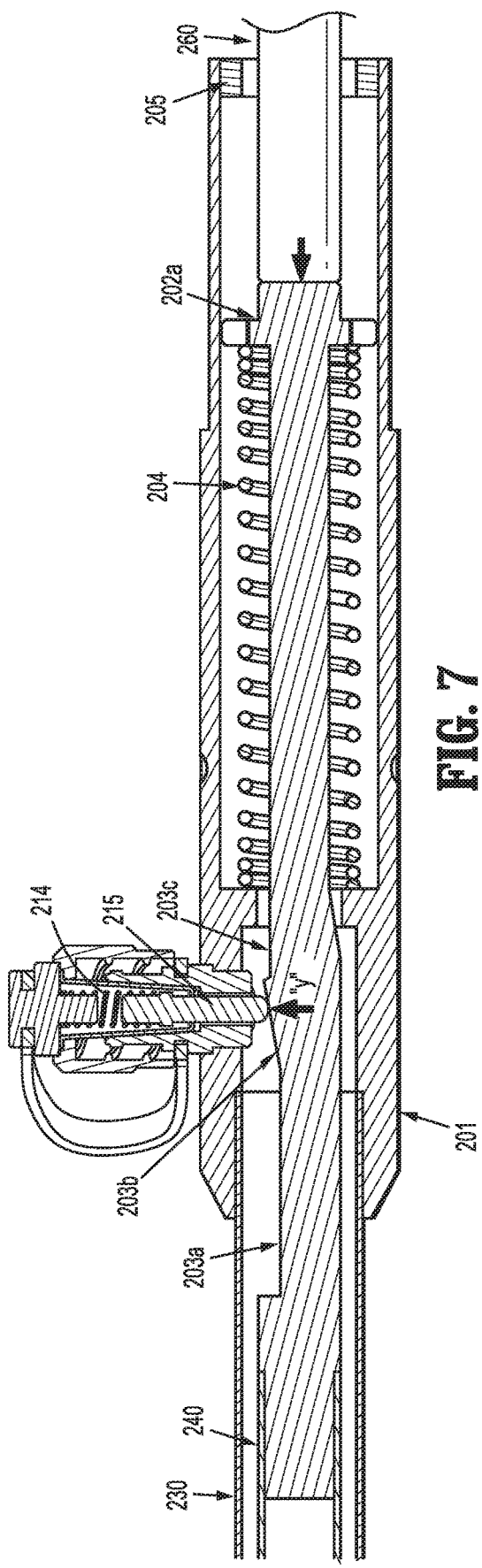
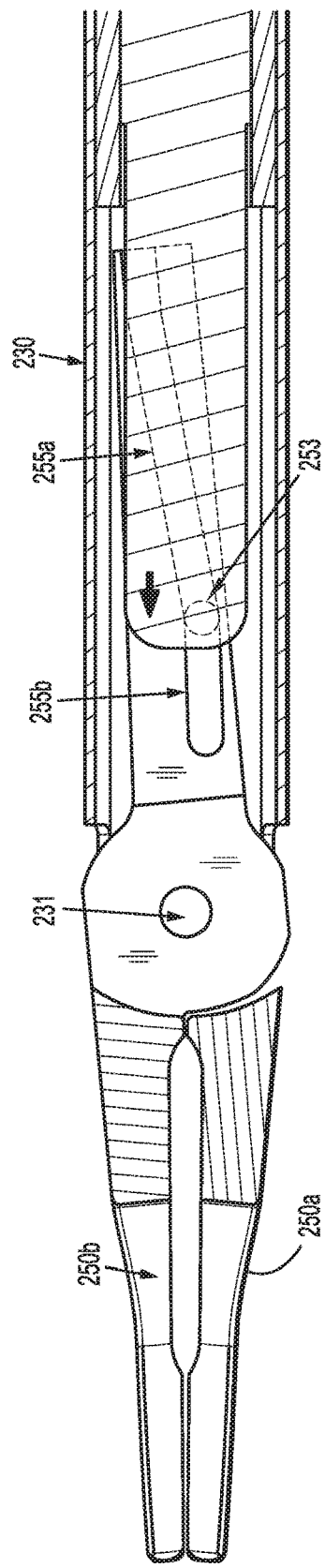
FIG. 7
FIG. 8

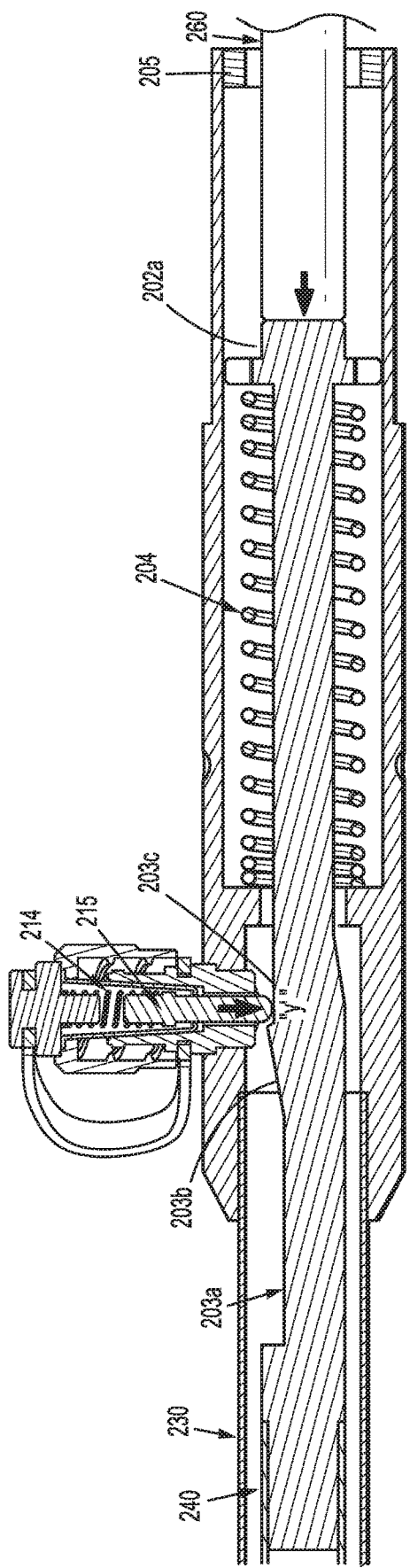
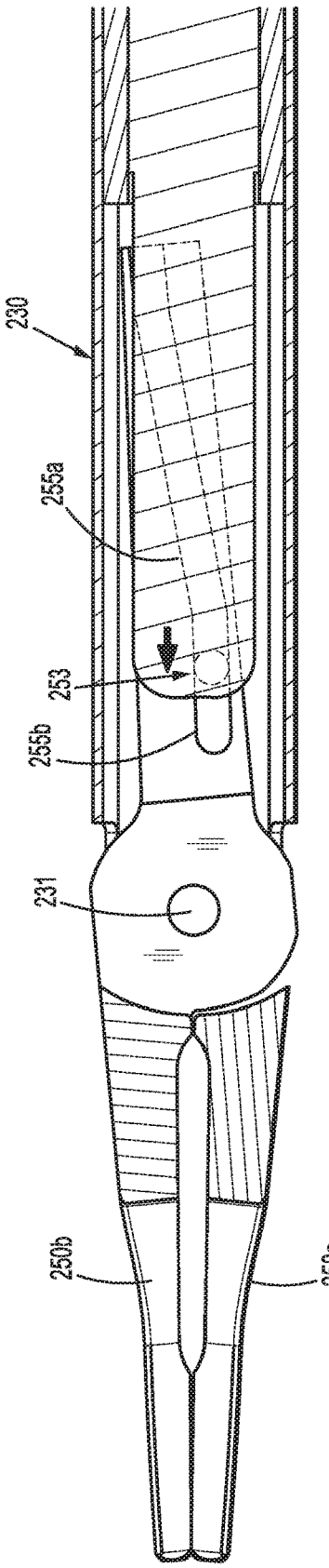
FIG. 9
FIG. 10

SURGICAL CLIP APPLIER WITH USER FEEDBACK FEATURE

CROSS-REFERENCE TO RELATED APPLICATIONS

This application is a National Stage Application of PCT/CN2017/072960 under 35 USC § 371 (a), the disclosure of the above-identified application is hereby incorporated by reference in its entirety.

BACKGROUND

1. Technical Field

The present disclosure generally relates to surgical clip appliers, and more particularly, to clip appliers with user feedback features and the like.

2. Background of Related Art

Surgical clip appliers are used in a variety of surgical procedures. For example, during some procedures, the user, e.g., a clinician, must often terminate the flow of blood or another fluid through, e.g., one or more ducts or blood vessels. The clinician will often use a surgical clip applier to apply a surgical clip to the blood vessel to prevent the flow of fluids therethrough during the procedure. Once applied to the vessel, the compressed clip terminates the flow of fluid therethrough. Surgical clip appliers typically include a housing, a handle assembly, a shaft extending from the handle assembly containing a plurality of clips therein, and a pair of jaws disposed on the distal end of the shaft for forming the clip around a vessel. Access to the interior of a patient's body is achieved through a small entrance incision made in the skin, through which the shaft of the clip applier is inserted for application of the clip onto and/or around the vessel to be occluded.

During these procedures, it is often desirable to ensure that the clip has been formed around or fired onto a vessel. Accordingly, a need exists for a surgical clip applier that provides feedback to the clinician that the clip has been formed or fired onto a vessel.

SUMMARY

The present disclosure relates to surgical clip appliers that provide audible and tactile feedback to a user when a clip has been applied.

According to an aspect of the present disclosure, a surgical clip applier is provided, including a handle assembly having a housing, a trigger, and an advancing mechanism supported in the housing and actuatable by the trigger. An elongated tube assembly extends from the housing. A first shaft is slidably disposed within the elongated tube assembly, the first shaft defining a surface portion. A second shaft is disposed through an outer surface of the elongated tube assembly and in operative engagement with the surface portion of the first shaft. Upon actuating the trigger, the advancing mechanism moves the first shaft distally within the elongated tube assembly relative to the second shaft such that the surface portion of the first shaft traverses the second shaft to produce at least one of an audible or tactile feedback.

In embodiments, a luer connector assembly may be disposed on the outer surface of the elongated tube assembly, the luer connector assembly including a biasing member operatively connected to the second shaft. The luer connector assembly may include a luer taper, a body, and a cap, the cap configured for removal from the body of luer connector assembly. The luer connector assembly may be configured for removal from the elongated tube assembly for maintenance of the elongated tube assembly. The surface portion of the first shaft may include a planar distal surface, a planar proximal surface, and a ramped surface disposed therebetween, wherein the ramped surface has a greater maximum height than the planar distal surface and the planar proximal surface. When the trigger is in an unactuated position, the second shaft of the luer connector assembly may be disposed over the planar distal surface of the first shaft. Upon a partial actuation of the trigger, the advancing mechanism of the handle assembly may urge the first shaft of the elongated tube assembly distally such that the ramped surface of the first shaft urges the second shaft to move within the luer connector assembly, wherein movement of the second shaft causes the biasing member to compress and load the second shaft with potential energy. Upon a full actuation of the trigger, the advancing mechanism of the handle assembly may urge the first shaft of the elongated tube assembly further distally until the ramped surface of the first shaft moves distal of the second shaft, whereupon the biasing member may expand and release the potential energy and cause the second shaft to impact the planar proximal surface of the first shaft. When the biasing member releases the potential energy and causes the second shaft to impact the planar proximal surface of the first shaft, at least one of the audible or tactile feedback may be produced.

In embodiments, the elongated tube assembly may include a drive rod disposed within the elongated tube assembly, the drive rod having a proximal end connected to a distal end of the first shaft, a yoke connected to a distal end of the drive rod, and a pair of jaw members supported at a distal end of the elongated tube assembly, at least one jaw member of the pair of jaw members connected to the yoke. The yoke may include a camming feature, wherein the at least one jaw member of the pair of jaw members defines a camming feature, and wherein the camming feature of the yoke is in operative association with the camming feature of the at least one jaw of the pair of jaw members. Upon an actuation of the trigger, the camming feature of the yoke may engage the camming feature of the at least one jaw member of the pair of jaw members to approximate the pair of jaw members relative to one another. A complete approximation of the pair of jaw members may occur simultaneously with at least one of the audible or tactile feedback.

In embodiments, the first shaft may include a flange portion at a proximal end thereof, and a tubular portion disposed between the flange portion and the surface portion. The first shaft may be disposed in a proximal shaft portion of the elongated tube assembly. The proximal shaft portion of the elongated tube assembly may include a stopper supported at a proximal end thereof and an inner wall located at a distal portion thereof. The elongated tube assembly may include a spring disposed over the first shaft between the flange portion of the first shaft, and the inner wall of the proximal shaft portion. Upon actuation of the trigger, the advancing mechanism may urge the first shaft distally and cause the spring to compress between the flange portion of the first shaft and the inner wall of the proximal shaft portion. Upon a full release of the trigger, the spring may bias the first shaft proximally such that the flange portion of the first shaft engages the stopper of the proximal shaft portion.

According to another aspect of the present disclosure, an elongated tube assembly configured for use with and selective connection to a handle assembly of a surgical instrument is provided, the elongated tube assembly including a proximal shaft portion, and an elongated outer tube extending distally from the proximal shaft portion. A first shaft is slidably disposed within the proximal shaft portion, the first shaft including a surface portion having a planar distal surface, a planar proximal surface, and a ramped surface disposed therebetween, wherein the ramped surface has a greater maximum height than the planar distal surface and the planar proximal surface. A luer connector assembly is disposed on an outer surface of the proximal shaft portion, the luer connector assembly including a second shaft, the second shaft extending into the proximal shaft portion and in operative engagement with the surface portion of the first shaft, whereupon distal movement of the first shaft causes the surface portion of the first shaft to traverse the second shaft of the luer connector assembly to produce at least one of an audible or tactile feedback.

In embodiments, the luer connector assembly may include a biasing member operatively connected to the second shaft. Distal movement of the first shaft may cause the ramped surface of the surface portion of the first shaft to move the second shaft within the luer connector assembly, wherein movement of the second shaft causes the biasing member to compress and load the second shaft with potential energy. Further distal movement of the first shaft may cause the ramped surface of the surface portion of the first shaft to move distally of the second shaft, whereupon the biasing member may expand and release the potential energy and cause the second shaft to impact the planar proximal surface of the first shaft. When the biasing member releases the potential energy and causes the second shaft to impact the planar proximal surface of the first shaft, at least one of the audible or tactile feedback may be produced.

BRIEF DESCRIPTION OF THE DRAWINGS

Objects and features of the present disclosure will become apparent to those of ordinary skill in the art when descriptions of various embodiments thereof are read with reference to the accompanying drawings, of which:

FIG. 2 is a perspective view, with parts separated, of an elongated tube assembly of the surgical clip applier of FIG. 1;

FIG. 2A is an enlarged view of the indicated area of detail of FIG. 2, further illustrating jaw members of the elongated tube assembly of FIG. 2;

FIG. 5 is an enlarged, cross-sectional view of a proximal portion of the elongated tube assembly of FIG. 3, as indicated in FIG. 3;

FIG. 6 is a partial, cross-sectional view of the distal portion of the elongated tube assembly of FIG. 1 with the jaw members in an open position, as taken through 6-6 of FIG. 4;

FIG. 7 is a partial, cross-sectional view of the proximal portion of the elongated tube assembly of FIG. 1 with a feedback shaft partially engaged by an actuation member;

FIG. 8 is a partial, cross-sectional view of the distal portion of the elongated tube assembly of FIG. 1 with the jaw members in a nearly closed position;

FIG. 9 is a partial, cross-sectional view of the distal portion of the elongated tube assembly of FIG. 1 with the feedback shaft fully engaged by the actuation member; and FIG. 10 is a partial, cross-sectional view of the distal portion of the elongated tube assembly of FIG. 1 with the jaw members in a fully closed position.

DETAILED DESCRIPTION

Figure 1:
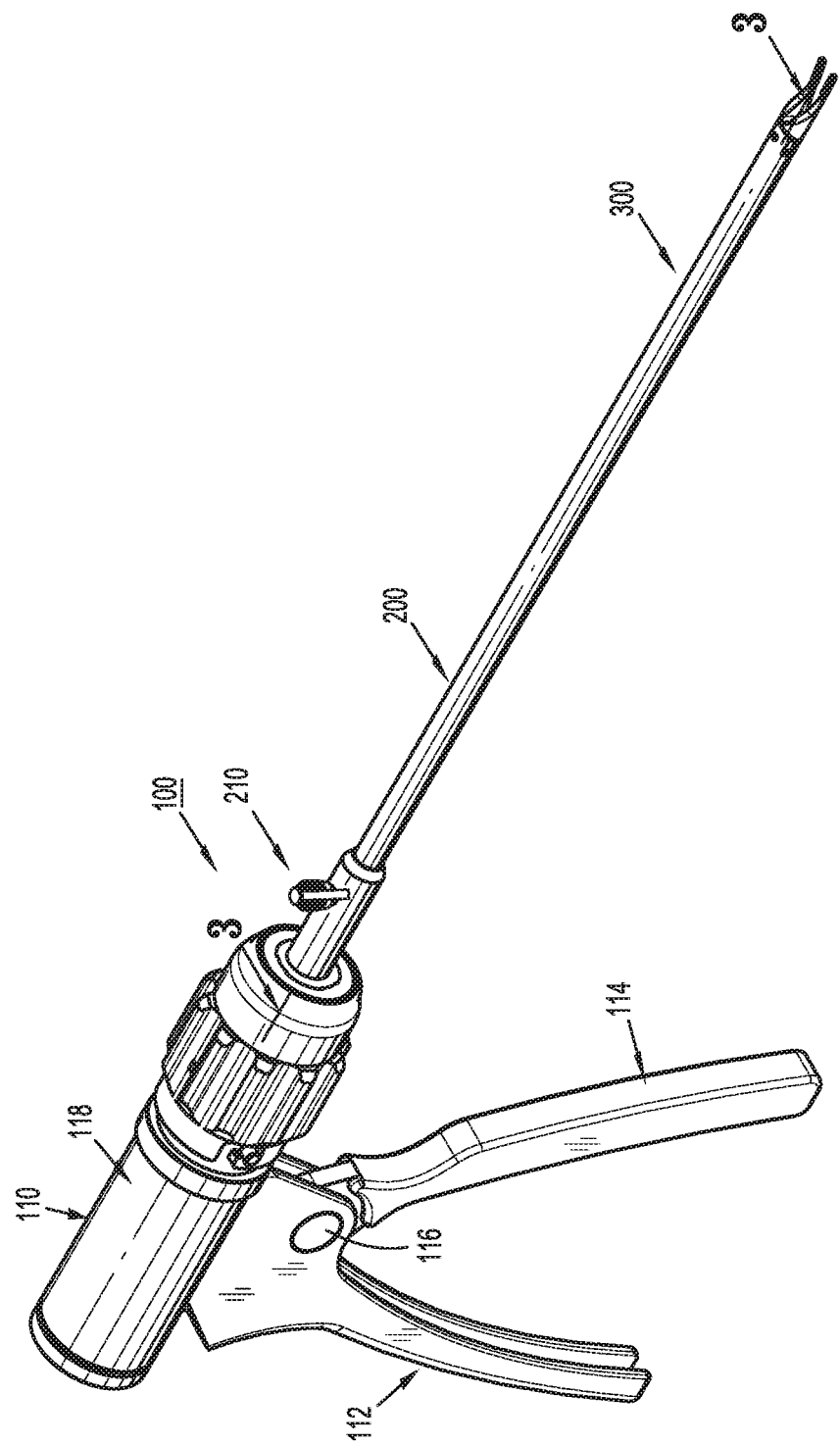
FIG. 1 is a perspective view of a surgical clip applier in accordance with the present disclosure.

The present disclosure is directed to a surgical clip applier that provides improved feedback to a clinician when firing a clip onto a vessel or the like. Specifically, the surgical clip applier described herein provides tactile and/or auditory feedback (e.g., a vibration through the surgical clip applier and/or an audible "click") to alert the clinician that a clip has been fired and/or fully formed. These and other aspects and features of the present disclosure are detailed herein below.

Embodiments of surgical clip appliers, in accordance with the present disclosure, will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the clinician and the term "distal" refers to the end of the apparatus which is further away from the clinician. Aspects and features of the surgical clip applier depicted herein, not germane to the understanding of the present disclosure, are omitted to avoid obscuring the aspects and features of the present disclosure in unnecessary detail.

Referring initially to FIG. 1, a surgical clip applier in accordance with the present disclosure is shown and generally designated as 100. Surgical clip applier 100 includes a handle assembly 110, an elongated tube assembly 200 projecting from handle assembly 110, a luer connector assembly 210 disposed on the elongated tube assembly 200, and a pair of jaw members 250a and 250b disposed on a distal end of the elongated tube assembly 200. Handle assembly 110 includes a fixed handle 112 and a squeezable trigger 114 pivotally attached to fixed handle 112 at pivot shaft 116. A housing or barrel 118 is supported on fixed handle 112 and is configured to selectively, removably receive a proximal end of elongated tube assembly 200. A plurality of surgical clips (not explicitly shown) are loaded into a clip cartridge assembly 300 disposed within elongated tube assembly 200. In operation, as trigger 114 of handle assembly 110 is actuated, a single surgical clip is fired and formed, e.g., around the vessel to be occluded. For a more detailed disclosure of endoscopic clip appliers, drive assemblies, and clip cartridge assemblies, reference may be made to commonly-assigned U.S. Pat. Nos. 5,084,057 and 5,100,420 to Green et al., U.S. Pat. No. 5,607,436 to Pratt et al., U.S. Pat. No. 5,695,502 to Pier et al., and U.S. Pat. No. 8,894,665 to Sorrentino et al., the disclosures of which are hereby incorporated by reference herein in their entirety.

Figure 2B:
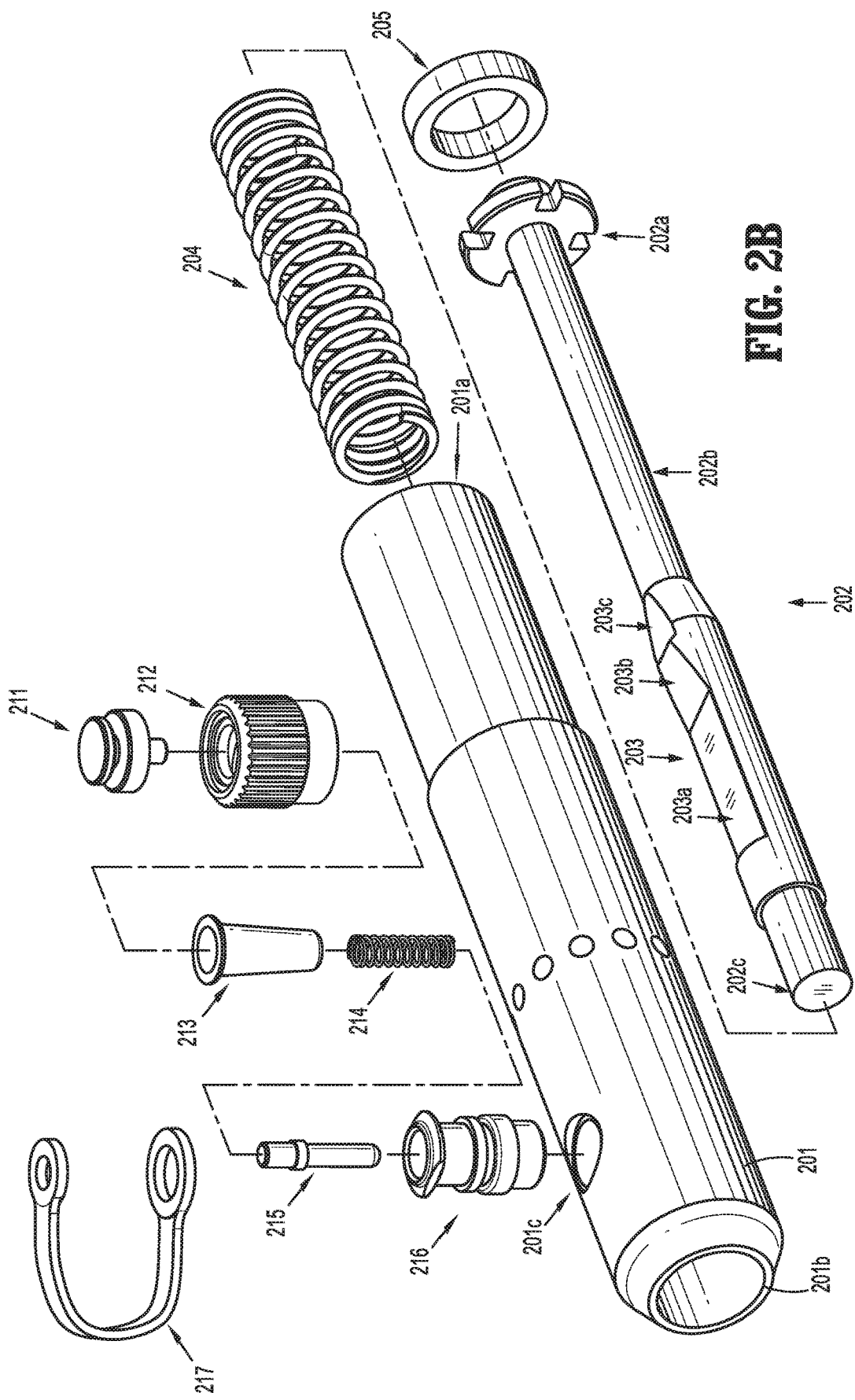
FIG. 2B is an enlarged view of the indicated area of detail of FIG. 2, further illustrating a luer connector assembly of the elongated tube assembly of FIG. 2.

Referring now to FIGS. 2, 2A, and 2B, an exploded view of the elongated tube assembly 200 is shown. Elongated tube assembly 200 includes a proximal shaft portion or luer housing 201. A proximal end 201a of luer housing 201 is connectable to handle assembly 110 and a distal end portion 201b of luer housing 201 is affixed to a proximal end 230a of an elongated outer tube 230 of elongated tube assembly 200. Elongated tube assembly 200 includes a feedback shaft 202, a spring or biasing member 204 disposed within luer housing 201, and a stopper 205.

Elongated tube assembly 200 includes a luer connector assembly 210 tangentially or perpendicularly affixed to a bore 201c defined in a surface of luer housing 201. Luer connector assembly 210 includes a cap 211 removably disposed on a body 212 defining a lumen therein, a luer taper or cone 213 disposed within body 212, a spring or biasing member 214, a shaft 215 disposed partially within biasing member 214, a fitting 216 disposed on luer housing 201, and a strap 217 connected to the cap 211. As will be described in greater detail below, biasing member 214 keeps shaft 215 projecting into luer housing 201 and in contact with feedback shaft 202. Upon a depression of trigger 114 of handle assembly 110, feedback shaft 202 is urged axially and distally within luer housing 201, which causes shaft 215 of luer connector assembly 210 to slide or travel along a feedback surface 203 of feedback shaft 202 (or, e.g., in general relative terms, distally moving feedback shaft 202 to induce movement of shaft 215) (FIGS. 5, 7 and 9), creating, e.g., a vibration or tactile impact within surgical clip applier 100 or auditory "click" to alert a clinician that a clip has been ejected from jaw members 250a, 250b and formed.

Figure 3:
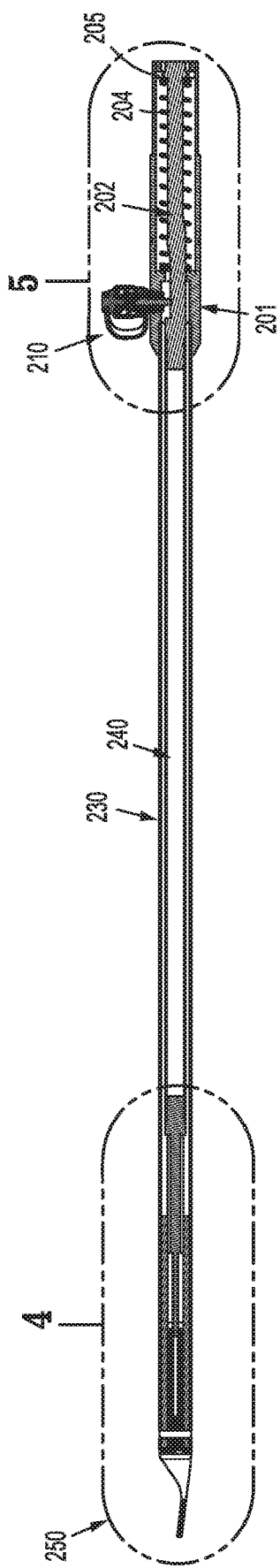
FIG. 3 is cross-sectional, elevational view of the elongated tube assembly of FIG. 1, as taken through 3-3 of FIG. 1.
Figure 4:
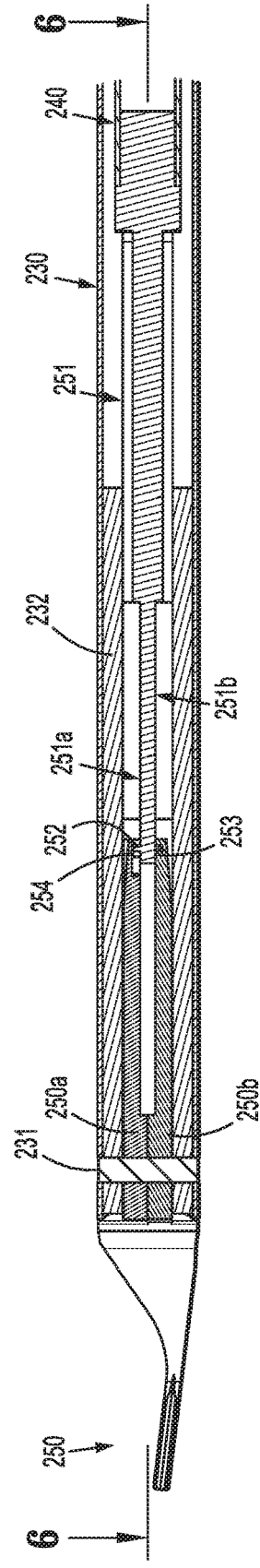
FIG. 4 is an enlarged, cross-sectional view of a distal portion of the elongated tube assembly of FIG. 3, as indicated in FIG. 3.

With reference to FIGS. 2-2B, 5, 7, and 9, feedback shaft 202 includes a proximal portion or flange 202a, a shaft portion 202b, and a distal end portion 202c. Feedback shaft 202 includes a feedback surface 203 disposed between shaft portion 202b and distal end portion 202c thereof. Feedback surface 203 includes a substantially planar or flat surface 203a, a ramped surface 203b disposed proximal of flat surface 203a, and a planar or drop surface 203c disposed proximal of ramped surface 203b. The ramped surface 203b may have a greater maximum height than the planar surface 203a and the drop surface 203c. As shown in FIGS. 3 and 5, feedback shaft 202 is slidably disposed within luer housing 201. Biasing member 204 of elongated tube assembly 200 is at least partially disposed over feedback shaft 202 and in compression between flange 202a of feedback shaft 202 and a wall 201d of (and within) luer housing 201. Stopper 205 of elongated tube assembly 200 is affixed to proximal end 201a of luer housing 201 and in abutment with flange 202a of feedback shaft 202. Stopper 205 prevents feedback shaft 202 from moving further proximally beyond proximal end 201a of luer housing 201.

With reference to FIGS. 3 and 5, feedback shaft 202 is shown in a rest or initial position wherein trigger 114 of handle assembly has not yet been actuated by the clinician. As will be described in further detail below, upon an actuation of trigger 114 of handle assembly 110, an actuation shaft 260 of handle assembly 110 (FIGS. 7 and 9) abuts and urges feedback shaft 202 axially and distally through luer housing 201.

With reference to FIG. 5, when feedback shaft 202 of elongated tube assembly 200 is in the rest position, shaft 215 of luer connector assembly 210 is in contact with flat surface 203a of feedback surface 203 of feedback shaft 202. In the rest or initial position, biasing member 214 of luer connector assembly 210 may be at rest or under slight compression between cap 211 and shaft 215 of luer connector assembly 210. With reference to FIG. 7, upon an initial or partial actuation of trigger 114 of handle assembly 110, actuation shaft 260 urges feedback shaft 202 distally into a partially actuated position. In the partially actuated position, feedback shaft 202 has been urged distally such that ramped surface 203b of feedback surface 203 thereof has been brought into engagement with shaft 215 of luer connector assembly 210 and causes shaft 215 to move upwards (e.g., radially outward) in direction "Y" and thereby compress spring 214 such that spring 214 is loaded with or increases in potential energy. With spring 214 in compression, a constant downward force is exerted or loaded onto shaft 215, which is then exerted or loaded onto ramped surface 203a of feedback surface 203 of feedback shaft 202.

Referring now to FIG. 9, upon a full actuation of trigger 114 of handle assembly 110, actuation shaft 260 urges feedback shaft 202 into a fully actuated position upon which shaft 215 of luer connector assembly 210 traverses ramped surface 203b of feedback surface 203 of feedback shaft 202 and falls onto drop surface 203c of feedback surface 203 of feedback shaft 202. Upon traversing ramped surface 203b and falling onto drop surface 203c of feedback surface 203 of feedback shaft 202, spring 214 releases its potential energy or force and shaft 215 "snaps" downward in a direction "Y'," to impact drop surface 203c. As will be described in detail below, the "snap" or impact by shaft 215 of luer connector assembly 210 onto drop surface 203c causes a vibration through surgical clip applier 100 and/or an auditory "click" to alert the clinician that a clip has been fired from surgical clip applier 100, or that surgical clip applier 100 has been fully actuated.

As can be appreciated, spring 214 of luer connector assembly 210 may have any suitable spring constant for producing tactile and/or audio feedback, e.g., a vibration through surgical clip applier 100 and/or an auditory "click." A clinician may disengage cap 211 from body 212 of luer connector assembly 210, whereupon spring 214 may be removed and replaced with another suitable spring, e.g., with a different spring constant. Likewise, shaft 215 of luer connector assembly 210 may be removed and replaced with another shaft e.g., of a different size, material, rigidity, or other material property capable of inducing audio and tactile feedback to a clinician.

In addition, cap 211, spring 214, and/or shaft 215 of luer connector assembly 210 may be removed from body 212 of luer connector assembly 210 such that a cleaning agent or another device may be inserted through cone 213, e.g., for cleansing and/or maintenance of elongated tube assembly 200 surgical clip applier 100. For example, water may be flushed into luer connector assembly 210 to clean elongated tube assembly 200. Additionally or alternatively, a flexible cleaning brush may be inserted through luer connector assembly 210 and through elongated tube assembly 200 for cleaning therewith. If necessary, the entire luer connector assembly 210 may be removed from luer housing 201 by removing fitting 216 from bore 201c of luer housing 201. As such, luer connector assembly 210 operates as a functional (but modified) luer connector.

It should be appreciated that luer connector assembly 210 and its components may be formed of metal, plastic, ceramic, polymer, composite, or any other suitable material, e.g., plastic, stainless steel, or the like. Likewise, components of luer connector assembly 210 may be interchangeable with commonly used luer components, e.g., luer tapers, fittings, caps, straps, locks, and the like.

Referring now to FIGS. 2, 5, 7, and 9, distal end 202c of feedback shaft 202 is shown coupled to a proximal end 240a of drive rod 240 of elongated tube assembly 200. Drive rod 240 of elongated tube assembly 200 is disposed within and aligned coaxially with elongated outer tube 230 of elongated tube assembly 200. As will be described below, as feedback shaft 202 moves from the rest or initial position to the actuated position, drive rod 240 is urged distally to actuate the jaw members 250a, 250b.

With reference to FIGS. 2, 4, 6, 8, and 10, a distal end 240b of drive rod 240 is coupled to a proximal portion 251a of a yoke 251 of elongated tube assembly 200. A distal portion 251b of yoke 251 includes a camming feature or first detent 252 disposed on a first side 251c thereof and a camming feature or second detent 253 disposed on a second side 251d thereof. First and second detents 252, 253 of yoke 251 are dimensioned to engage a camming feature or cam slots 254, 255 of the jaw members 250a, 250b, respectively. More particularly, first detent 252 of yoke 251 slidably engages cam slot 254 of jaw member 250a and second detent 253 slidably engages cam slot 255 of jaw member 250b. The detent and cam slot combination work together as a cam follower mechanical linkage. In operation, the linear and distal motion of drive rod 240 moves yoke 251 distally causing detents 252, 253 to slide within their respective cam slots 254, 255 of the jaw members 250a, 250b, which causes the jaw members 250a, 250b to, e.g., close or move in a generally arcuate fashion away from each other. As will be fully described below, upon an actuation of trigger 114, the audible and tactile feedback provided to a clinician via shaft 215 of luer connector assembly 210 along feedback shaft 202, corresponds to the movement of the jaw members 250a, 250b and alerts the clinician to the firing and formation of a single clip.

The jaw members 250a, 250b of elongated tube assembly 200 may be disposed at least partially within a jaw housing 232, which is disposed within a distal portion of elongated outer tube 230. Elongated outer tube 230 includes a through-hole 230a aligned with through-hole 232a of jaw housing 232 of elongated outer tube assembly 200, which is also aligned with through-holes 250c, 250d of the jaw members 250a, 250b, respectively. A pivot pin 231 is inserted into through-holes 230a of elongated outer tube 230, through-holes 232a of jaw housing 232, and through holes 250c, 250d of the jaw members 250a, 250b, which permits the jaw members 250a, 250b to pivot, e.g., open and close about pivot pin 231.

Referring to FIGS. 5 and 6, elongated tube assembly 200 of surgical instrument 100 is shown in the rest or initial position. As described above, in the rest or initial position, shaft 215 of luer connector assembly 210 is disposed on flat surface 203a of feedback surface 203 of feedback shaft 202. In this position, the jaw members 250a, 250b are shown in a default open position wherein detent 253 of the yoke 251 is disposed within a proximal most portion of cam-slot 255 (FIG. 6) of jaw member 250b and detent 252 is disposed within a proximal most portion of cam-slot 254 of jaw member 250a (not explicitly shown).

Now referring to FIGS. 7 and 8, as described above, a clinician partially depresses or actuates trigger 114, which causes actuation shaft 260 to urge feedback shaft 202 distally through luer housing 201 into the partially actuated position. As described above, in the partially actuated position, feedback shaft 202 is urged distally such that ramped surface 203b of feedback surface 203 thereof causes shaft 215 of luer connector assembly 210 to move upwards or vertically in direction "Y" and compress spring 214 such that spring 214 is loaded with or increases in potential energy. Distal movement of feedback shaft 202 urges drive rod 240 distally, which in turn urges yoke 251 distally. As yoke 251 is urged distally, detents 252, 253 thereof are moved distally within cam-slots 254, 255 of the jaw members 250a, 250b, respectively. Cam-slots 254, 255 of the jaw members 250a, 250b have proximal sloping portions 254a, 255a, respectively. In use, as detents 252, 253 of yoke 251 travel through proximal sloping portions 254a, 255a of cam slots 254, 255 of the jaw members 250a, 250b, the jaw members 250a, 250b are urged from their default open position, as shown in FIG. 6, into a nearly closed position, as shown in FIG. 8.

With reference to FIGS. 9 and 10, upon a full actuation of trigger 114 (e.g., to the fully actuated position) of handle assembly 110, detents 252, 253 of yoke 251 are urged further distally into distal sloping portions 254b, 255b of cam slots 254, 255 of the jaw members 250a, 250b, respectively. Travel of detents 252, 253 of yoke 251 within distal sloping portions 254b, 255b of cam-slots 254, 255 causes the jaw members 250a, 250b to fully close and form a clip. Simultaneously, actuation shaft 260 urges feedback shaft 202 further distally until shaft 215 of luer connector assembly 210 traverses step surface 203b onto drop surface 203c of feedback shaft 202, which, as described above, provides auditory and tactile feedback to the clinician that the clip has been fired and formed. As such, the clinician is alerted when the energy of spring 214 is released onto shaft 215 of luer connector assembly 210, which energy is also released onto drop surface 203c of feedback shaft 202. The release of energy and downward movement of shaft 215 in direction "Y" induces a vibration within feedback shaft 202, elongated tube assembly 200, and handle assembly 110, which is then absorbed and felt by the clinician, e.g., through the clinician's hand. In addition, the clinician hears an auditory "click" and is alerted that the clip has been fired from surgical clip applier 100. Upon a full actuation of trigger 114, biasing member 204 of elongated tube assembly 200 is compressed. More particularly, upon actuation of the trigger 114, the actuation shaft 260 urges feedback shaft 202 distally and causes the spring 204 to compress between the flange 202a of feedback shaft 202 and the wall 201d of the luer housing 201.

After the clip has been released from surgical clip applier 100, the clinician releases trigger 114, upon which biasing member 204 of elongated tube assembly 200 expands and causes feedback shaft 202 to "reset" to the rest or initial position (FIG. 5), such that shaft 215 is again disposed over flat surface 203a of feedback surface 203 of feedback shaft 202. Thus, each time surgical clip applier 100 ejects a clip and completes a firing cycle (e.g., transitions from the rest or initial position to the fully actuated position), the clinician will be alerted to a corresponding vibration or auditory "click" as shaft 215 of luer connector 210 must again traverse feedback surface 203 of feedback shaft 202.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:
1. A surgical clip applier, comprising:
    a handle assembly including a housing, a trigger, and an advancing mechanism supported in the housing and being actuatable by the trigger;
    an elongated tube assembly extending from the housing;

a first shaft slidably disposed within the elongated tube assembly, the first shaft defining a surface portion; and
a second shaft disposed through an outer surface of the elongated tube assembly and in operative engagement with the surface portion of the first shaft,
wherein, upon actuating the trigger, the advancing mechanism moves the first shaft distally within the elongated tube assembly relative to the second shaft such that the surface portion of the first shaft traverses the second shaft to produce at least one of an audible or tactile feedback.

2. The surgical clip applier of claim 1, further comprising a luer connector assembly disposed on the outer surface of the elongated tube assembly, the luer connector assembly including a biasing member operatively connected to the second shaft.

3. The surgical clip applier of claim 2, wherein the surface portion of the first shaft includes a planar distal surface, a planar proximal surface, and a ramped surface disposed therebetween, wherein the ramped surface has a greater maximum height than the planar distal surface and the planar proximal surface.

4. The surgical clip applier of claim 3, wherein, when the trigger is in an unactuated position, the second shaft is disposed over the planar distal surface of the first shaft.

5. The surgical clip applier of claim 4, wherein, upon a partial actuation of the trigger, the advancing mechanism of the handle assembly urges the first shaft of the elongated tube assembly distally such that the ramped surface of the first shaft urges the second shaft to move within the luer connector assembly, wherein movement of the second shaft causes the biasing member to compress and load the second shaft with potential energy.

6. The surgical clip applier of claim 5, wherein, upon a full actuation of the trigger, the advancing mechanism of the handle assembly urges the first shaft of the elongated tube assembly further distally until the ramped surface of the first shaft moves distal of the second shaft, whereupon the biasing member expands and releases the potential energy and causes the second shaft to impact the planar proximal surface of the first shaft.

7. The surgical clip applier of claim 6, wherein when the biasing member releases the potential energy and causes the second shaft to impact the planar proximal surface of the first shaft, at least one of the audible or tactile feedback is produced.

8. The surgical clip applier of claim 7 further comprising:
a drive rod disposed within the elongated tube assembly, the drive rod having a proximal end connected to a distal end of the first shaft;
a yoke connected to a distal end of the drive rod; and
a pair of jaw members supported at a distal end of the elongated tube assembly, at least one jaw member of the pair of jaw members connected to the yoke.

9. The surgical clip applier of claim 8, wherein the yoke includes a camming feature, wherein the at least one jaw member of the pair of jaw members defines a camming feature, and wherein the camming feature of the yoke is in operative association with the camming feature of the at least one jaw member of the pair of jaw members.

10. The surgical clip applier of claim 9, wherein, upon the actuating of the trigger, the camming feature of the yoke engages the camming feature of the at least one jaw member of the pair of jaw members to approximate the pair of jaw members relative to one another.

11. The surgical clip applier of claim 10, wherein a complete approximation of the pair of jaw members occurs simultaneously with at least one of the audible or tactile feedback.

12. The surgical clip applier of claim 2, wherein the luer connector assembly further includes a luer taper, a body, and a cap, the cap configured for removal from the body of the luer connector assembly.

13. The surgical clip applier of claim 12, wherein the luer connector assembly is configured for removal from the elongated tube assembly for maintenance of the elongated tube assembly.

14. The surgical clip applier of claim 1, wherein the first shaft includes:
a flange portion at a proximal end thereof; and
a tubular portion disposed between the flange portion and the surface portion.

15. The surgical clip applier of claim 14, wherein the first shaft is disposed in a proximal shaft portion of the elongated tube assembly.

16. The surgical clip applier of claim 15, wherein the proximal shaft portion of the elongated tube assembly includes a stopper supported at a proximal end thereof and an inner wall located at a distal portion thereof.

17. The surgical clip applier of claim 16, the elongated tube assembly further comprising a spring disposed over the first shaft between the flange portion of the first shaft, and the inner wall of the proximal shaft portion.

18. The surgical clip applier of claim 17, wherein, upon the actuating of the trigger, the advancing mechanism urges the first shaft distally and causes the spring to compress between the flange portion of the first shaft and the inner wall of the proximal shaft portion.

19. The surgical clip applier of claim 18, wherein, upon a full release of the trigger, the spring biases the first shaft proximally such that the flange portion of the first shaft engages the stopper of the proximal shaft portion.

20. An elongated tube assembly configured for use with and selective connection to a handle assembly of a surgical instrument, the elongated tube assembly comprising:
a proximal shaft portion;
an elongated outer tube extending distally from the proximal shaft portion;
a first shaft slidably disposed within the proximal shaft portion, the first shaft including a surface portion having a planar distal surface, a planar proximal surface, and a ramped surface disposed therebetween, wherein the ramped surface has a greater maximum height than the planar distal surface and the planar proximal surface; and
a luer connector assembly disposed on an outer surface of the proximal shaft portion, the luer connector assembly including a second shaft, the second shaft extending into the proximal shaft portion and in operative engagement with the surface portion of the first shaft,
wherein distal movement of the first shaft causes the surface portion of the first shaft to traverse the second shaft of the luer connector assembly to produce at least one of an audible or tactile feedback.

21. The elongated tube assembly of claim 20, wherein the luer connector assembly includes a biasing member operatively connected to the second shaft.

22. The elongated tube assembly of claim 21, wherein the distal movement of the first shaft causes the ramped surface of the surface portion of the first shaft to move the second shaft within the luer connector assembly, wherein movement of the second shaft causes the biasing member to compress and load the second shaft with potential energy.

23. The elongated tube assembly of claim 22, wherein further distal movement of the first shaft causes the ramped surface of the surface portion of the first shaft to move distally of the second shaft, whereupon the biasing member expands and releases the potential energy and causes the second shaft to impact the planar proximal surface of the first shaft.

24. The elongated tube assembly of claim 23, wherein when the biasing member releases the potential energy and causes the second shaft to impact the planar proximal surface of the first shaft, at least one of the audible or tactile feedback is produced.

\* \* \* \* \*